(12) United States Patent
Smith

(10) Patent No.: US 8,517,918 B2
(45) Date of Patent: Aug. 27, 2013

(54) OPTICAL TROCAR WITH SCOPE HOLDING ASSEMBLY

(75) Inventor: Robert C. Smith, Chesire, CT (US)

(73) Assignee: Covidien LP, Mansfield, MA (US)

( * ) Notice: Subject to any disclaimer, the term of this patent is extended or adjusted under 35 U.S.C. 154(b) by 22 days.

(21) Appl. No.: 12/882,581

(22) Filed: Sep. 15, 2010

(65) Prior Publication Data
US 2011/0004061 A1 Jan. 6, 2011

Related U.S. Application Data

(63) Continuation of application No. 11/103,892, filed on Apr. 12, 2005, now Pat. No. 7,824,327.

(51) Int. Cl.
*A61B 1/04* (2006.01)
*A61B 1/00* (2006.01)
*A61M 5/178* (2006.01)

(52) U.S. Cl.
USPC .................. 600/114; 604/164.09; 604/167.06

(58) Field of Classification Search
USPC ................... 600/114; 604/167.01–167.06
See application file for complete search history.

(56) References Cited

U.S. PATENT DOCUMENTS

| | | | |
|---|---|---|---|
| 1,882,213 A | 10/1932 | Donovan | |
| 3,652,100 A | 3/1972 | Baturka | |
| 3,760,810 A | 9/1973 | Hoorn | |
| 4,607,619 A | 8/1986 | Seike et al. | |
| 4,700,694 A | 10/1987 | Shishido | |
| 4,705,023 A | 11/1987 | Arai | |
| 4,802,487 A | 2/1989 | Msertin et al. | |
| 4,878,485 A | 11/1989 | Adair | |
| 4,978,341 A * | 12/1990 | Niederhauser | 604/256 |
| 5,169,397 A | 12/1992 | Sakashita et al. | |
| 5,217,441 A | 6/1993 | Shichman | |
| 5,226,890 A | 7/1993 | Ianniruberto et al. | |
| 5,250,068 A | 10/1993 | Ideguchi et al. | |
| 5,261,891 A * | 11/1993 | Brinkerhoff et al. | 604/164.12 |
| 5,271,380 A * | 12/1993 | Riek et al. | 600/104 |
| 5,279,597 A | 1/1994 | Dassa et al. | |

(Continued)

FOREIGN PATENT DOCUMENTS

EP 0 426 407 5/1991
WO WO 03/026512 4/2003

OTHER PUBLICATIONS

European Search Report for EP 06006907, dated Dec. 12, 2006.

(Continued)

*Primary Examiner* — Alireza Nia

(57) ABSTRACT

An optical access apparatus for receiving an endoscope to permit visualization during passage through tissue includes an access member dimensioned for insertion through body tissue. The access member defines a longitudinal axis and has a longitudinal opening for receiving an endoscope. The access member has a closed penetrating end adapted to pass through tissue. The closed penetrating end is transparent to permit visualization of tissue with the endoscope. The optical access apparatus further includes a locking collet coaxially mounted relative to the longitudinal axis of the access member and a manual member mounted adjacent the locking collet and operatively engageable therewith. The locking collet has internal surfaces defining an internal passage to permit passage of the surgical instrument. The manual member is adapted for rotational movement about the longitudinal axis to reduce an internal dimension of the internal passage of the locking collet to cause the internal surfaces of the locking collet to securely engage the surgical instrument.

9 Claims, 13 Drawing Sheets

(56) References Cited

U.S. PATENT DOCUMENTS

| | | | |
|---|---|---|---|
| 5,290,276 A | | 3/1994 | Sewell |
| 5,300,035 A | * | 4/1994 | Clement .................. 604/167.01 |
| 5,334,150 A | | 8/1994 | Kaali |
| 5,336,206 A | | 8/1994 | Shichman |
| 5,354,302 A | | 10/1994 | Ko |
| 5,370,640 A | | 12/1994 | Kolff |
| 5,376,076 A | | 12/1994 | Kaali |
| 5,380,291 A | | 1/1995 | Kaali |
| 5,380,302 A | | 1/1995 | Orth |
| 5,385,572 A | | 1/1995 | Nobles et al. |
| 5,391,152 A | | 2/1995 | Patterson |
| 5,431,151 A | | 7/1995 | Riek et al. |
| 5,441,041 A | | 8/1995 | Sauer et al. |
| 5,445,142 A | | 8/1995 | Hassler |
| 5,467,762 A | | 11/1995 | Sauer et al. |
| 5,514,109 A | * | 5/1996 | Mollenauer et al. .......... 604/249 |
| 5,551,947 A | | 9/1996 | Kaali |
| 5,562,696 A | | 10/1996 | Nobles et al. |
| 5,569,160 A | | 10/1996 | Sauer et al. |
| 5,569,291 A | | 10/1996 | Priviter et al. |
| 5,569,292 A | | 10/1996 | Scwemberger et al. |
| 5,571,133 A | | 11/1996 | Yoon |
| 5,591,191 A | | 1/1997 | Kieturakis |
| 5,591,192 A | | 1/1997 | Priviter et al. |
| 5,601,559 A | | 2/1997 | Melker et al. |
| 5,609,562 A | | 3/1997 | Kaali |
| 5,620,188 A | | 4/1997 | McCurry et al. |
| 5,632,717 A | | 5/1997 | Yoon |
| 5,658,236 A | | 8/1997 | Sauer et al. |
| 5,658,306 A | | 8/1997 | Kieturakis et al. |
| 5,662,613 A | | 9/1997 | Astarita |
| 5,662,673 A | | 9/1997 | Kieturakis |
| 5,674,184 A | | 10/1997 | Hassler |
| 5,681,323 A | | 10/1997 | Arick |
| 5,685,820 A | | 11/1997 | Riek et al. |
| 5,716,369 A | | 2/1998 | Riza |
| 5,720,761 A | | 2/1998 | Kaali |
| 5,738,628 A | | 4/1998 | Sierocuk |
| 5,797,944 A | | 8/1998 | Nobles et al. |
| 5,817,061 A | | 10/1998 | Goodwin et al. |
| 5,843,115 A | | 12/1998 | Morejon |
| 5,857,999 A | | 1/1999 | Quick et al. |
| 5,860,996 A | | 1/1999 | Urban et al. |
| 5,873,889 A | | 2/1999 | Chin |
| 5,971,958 A | | 10/1999 | Zhang |
| 5,980,549 A | | 11/1999 | Chin |
| 6,007,481 A | | 12/1999 | Riek et al. |
| 6,039,725 A | | 3/2000 | Moenning et al. |
| 6,152,871 A | | 11/2000 | Foley et al. |
| 6,171,281 B1 | | 1/2001 | Zhang |
| 6,176,823 B1 | | 1/2001 | Foley et al. |
| 6,176,824 B1 | | 1/2001 | Davis |
| 6,203,557 B1 | | 3/2001 | Chin |
| 6,206,823 B1 | | 3/2001 | Kolata et al. |
| 6,209,886 B1 | | 4/2001 | Estes et al. |
| 6,228,059 B1 | | 5/2001 | Astarita |
| 6,245,011 B1 | | 6/2001 | Dudda et al. |
| 6,264,604 B1 | | 7/2001 | Kieturakis et al. |
| 6,336,914 B1 | | 1/2002 | Gillespie, III |
| 6,364,840 B1 | | 4/2002 | Crowley |
| 6,478,806 B2 | | 11/2002 | McFarlane |
| 6,685,630 B2 | | 2/2004 | Sauer et al. |
| 6,695,816 B2 | | 2/2004 | Cassidy |
| 6,719,772 B2 | | 4/2004 | Trask et al. |
| 2002/0072713 A1 | | 6/2002 | Almond |
| 2004/0236347 A1 | * | 11/2004 | Karasawa ..................... 606/108 |
| 2005/0065543 A1 | | 3/2005 | Kahle et al. |

OTHER PUBLICATIONS

European Search Report for EP 06006907, dated Aug. 3, 2006 (7 pages).

* cited by examiner

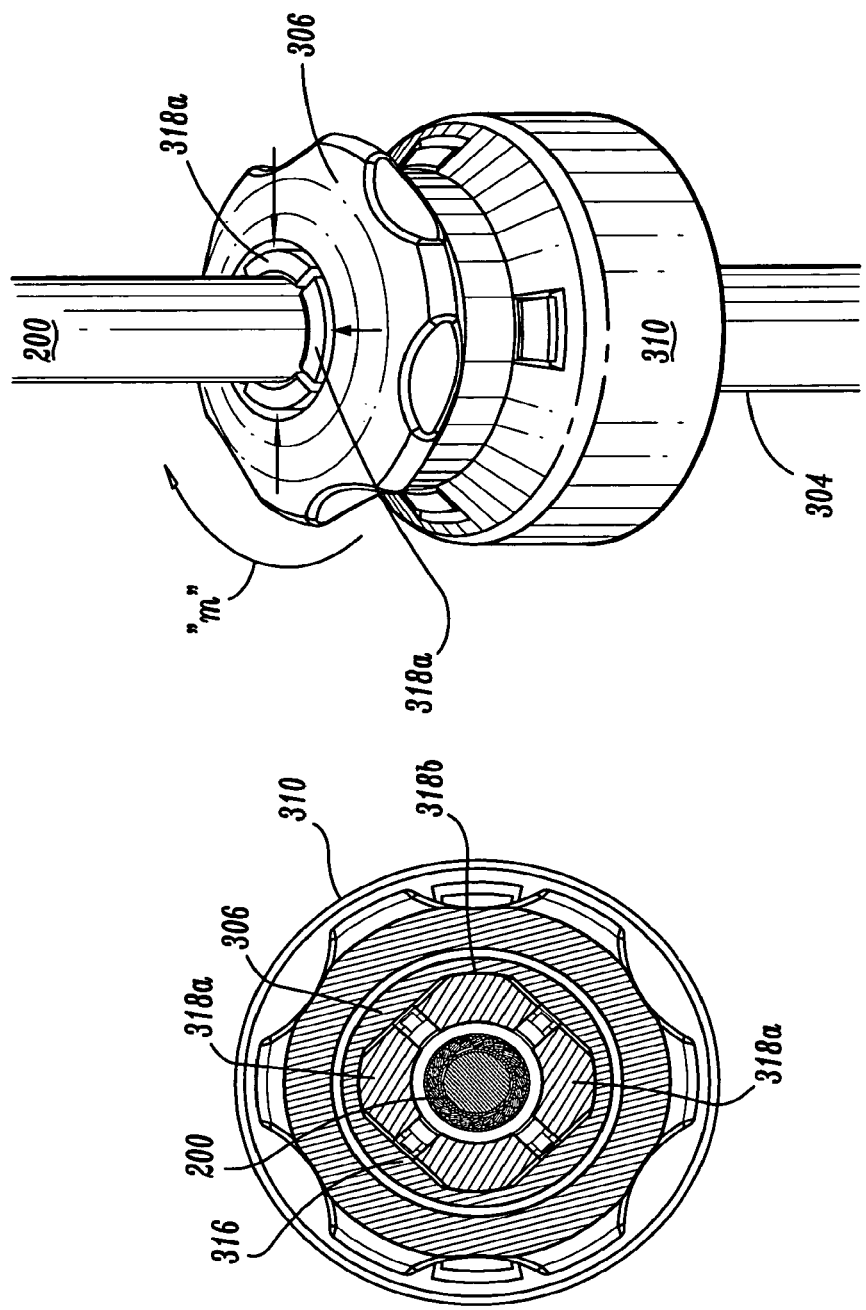

OPTICAL TROCAR WITH SCOPE HOLDING ASSEMBLY

CROSS-REFERENCE TO RELATED APPLICATIONS

The present application is a continuation of U.S. application Ser. No. 11/103,892, filed Apr. 12, 2005, the entire contents of the application being incorporated by reference herein.

BACKGROUND

1. Technical Field

The present invention relates to an apparatus for penetration of body tissue. More particularly, the present invention relates to an optical trocar including a scope holding mechanism for selectively securing an endoscope, laparoscope, or surgical instruments within the optical trocar to provide visualization during penetration of the peritoneum or other body tissue.

2. Background of Related Art

In endoscopic surgical procedures, surgery is performed in any hollow viscus of the body through a small incision or through narrow endoscopic tubes (cannulas) inserted through a small entrance wound in the skin. In laparoscopic procedures, surgery is performed in the interior of the abdomen. Laparoscopic and endoscopic procedures often require the surgeon to act on organs, tissues and vessels far removed from the incision, thereby requiring that any instruments used in such procedures be of sufficient size and length to permit remote operation. Typically, after the surgical region is insufflated, a trocar is used to puncture the body cavity and includes a cannula which remains in place for use during the laparoscopic procedure. Generally, a trocar includes a stylet or obturator having a sharp tip for penetrating the body cavity. An example of a known trocar is described in commonly assigned U.S. Pat. No. 4,601,710 to Moll. Most currently used trocars rely on protective tubes or relative retraction of the tip to prevent inadvertent contact with tissue.

SUMMARY

Accordingly, the present disclosure relates to further improvement in accessing/penetrating body tissue during a surgical procedure, preferably, a laparoscopic procedure. The present disclosure is directed to a surgical system including an optical trocar for directly observing the penetration of the peritoneum or other body portions. The optical trocar includes a transparent window for passing optical images to an imaging system of an endoscope or laparoscope positioned within the optical trocar. In addition, the present invention provides an improved penetrating end for penetration of body tissue.

In one preferred embodiment, an optical access apparatus for receiving an endoscope to permit visualization during passage through tissue includes an access member which is dimensioned for insertion through body tissue. The access member defines a longitudinal axis and has a longitudinal opening for receiving an endoscope. The access member has a closed penetrating end adapted to pass through tissue. The closed penetrating end is transparent to permit visualization of tissue with the endoscope. The optical access apparatus further includes a locking collet coaxially mounted relative to the longitudinal axis of the access member and a manual member mounted adjacent the locking collet and operatively engageable therewith. The locking collet has internal surfaces defining an internal passage to permit passage of the endoscope. The manual member is adapted for rotational movement about the longitudinal axis to reduce an internal dimension of the internal passage of the locking collet to cause the internal surfaces of the locking collet to securely engage the endoscope. The manual member may define a central aperture for at least partial reception of the locking collet.

In one embodiment, the locking collet is adapted for rotational movement relative to the longitudinal axis whereby rotational movement of the manual member causes the locking collet to correspondingly rotate. The locking collet is further adapted for longitudinal movement relative to the manual member. Preferably, the locking collet and the manual member include corresponding camming surfaces whereby upon longitudinal movement of the locking collet relative to the manual member the camming surfaces cooperate to reduce the internal dimension of the internal passage of the locking collet. Cam slot means for effecting longitudinal movement of the locking collet upon rotational movement thereof may also be provided.

In an alternate embodiment, the locking collet is fixed relative to the access member whereby the manual member is adapted to rotate about the locking collet. The locking collet and the manual member include corresponding camming surfaces whereby, upon rotational movement of the manual member relative to the collet, the camming surfaces cooperate to reduce the internal dimension of the internal passage of the locking collet.

The penetrating end defines a tapered configuration having opposed concave surfaces and opposed convex surfaces. This alternating concave and convex relationship provides a reduced profile to facilitate passage through tissue.

The present disclosure is also directed to a surgical system including an endoscope and an optical access apparatus for reception of the endoscope. The optical access apparatus includes a housing defining a longitudinal axis, a locking collet mounted to the housing and coaxially mounted relative to the longitudinal axis and having internal surfaces defining an internal passage to permit passage of the endoscope, and a manual member coaxially mounted about the locking collet. The manual member is adapted for rotational movement about the longitudinal axis to compress the locking collet to reduce an internal dimension of the internal passage of the locking collet to thereby cause the internal surfaces of the locking collet to securely engage the endoscope in frictional engagement therewith. The optical access apparatus also has an elongated access member extending from the housing and having a longitudinal opening for receiving the endoscope. The access member has a closed penetrating end adapted to pass through tissue. The closed penetrating end is transparent to permit visualization of tissue with the endoscope.

In one embodiment, the locking collet is adapted for rotational and longitudinal movement relative to the longitudinal axis whereby rotational movement of the manual member causes the locking collet to rotate and move in a longitudinal direction. The manual member preferably includes internal compressive surfaces adapted to engage the locking collet during longitudinal movement of the locking collet to reduce the internal dimension of the internal passage of the locking collet.

In another embodiment, the locking collet is fixed within the housing and the manual member is adapted to rotate about the locking collet. The manual member includes internal compressive surfaces adapted to engage the locking collet during rotational movement of the manual member to reduce the internal dimension of the internal passage of the locking collet. The manual member includes internal cam shelves.

The internal cam shelves are accommodated within outer recesses of the locking collet when in an initial position of the manual member whereby, upon rotational movement of the manual member to an actuated position, the cam shelves traverse the grooves to engage outer cam surfaces of the locking collet.

A method of using the system is also disclosed.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 19 is an axial cross-section view of the housing of the optical access apparatus in accordance with the embodiment of FIGS. 13-18 further illustrating the manual member in the initial position;

FIG. 20 is a view similar to the view of FIG. 17 illustrating movement of the manual member to the actuated position in accordance with the embodiment of FIGS. 13-19;

DESCRIPTION OF PREFERRED EMBODIMENTS

Figure 1:
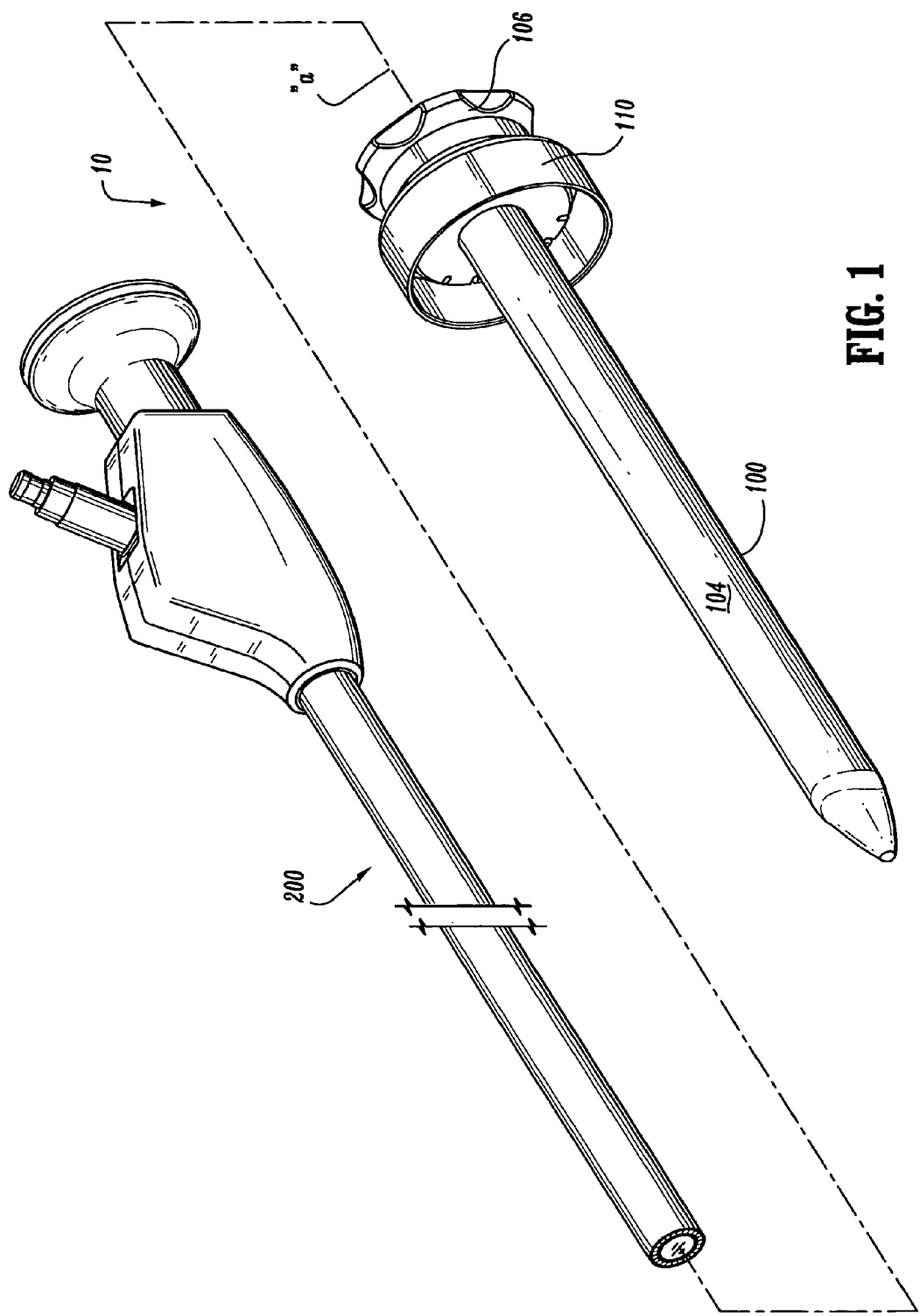
FIG. 1 is a perspective view of a surgical system in accordance with the principles of the present disclosure illustrating the optical access apparatus and an endoscope for insertion within the access apparatus.

Referring now to FIG. 1, there is illustrated a surgical system in accordance with the present disclosure. System 10 includes two components, namely, optical access apparatus 100 and endoscope 200 which is positionable within the access apparatus 100. System 10 has particular application in accessing the abdominal cavity during a laparoscopic procedure. Endoscope 200 is positioned within optical access apparatus 100 and the assembled unit is advanced through an incision and into the body cavity. During the advancement within tissue, endoscope 200 permits constant visualization of the neighboring tissue thereby providing confirmation upon entering into the body cavity while also preventing undesired contact or engagement with any underlying organs. Alternatively, endoscope 200 may be positioned within optical access apparatus 100 after the optical access apparatus 100 has been advanced into the body cavity.

Endoscope 200 may be any conventional scope suitable for endoscopic applications including, e.g., a laparoscope, arthroscope, colonoscope, etc. In one preferred embodiment, endoscope 200 may be the scope disclosed in commonly assigned U.S. Pat. No. 5,412,504 to Leiner, the entire contents of which disclosure are hereby incorporated by reference. Endoscope 200 incorporates an optical train or lens arrangement which is capable of transmitting an image of an object from the distal or objective lens through the eyepiece or monitor for viewing by the surgeon. Thus, although FIG. 1 shows an endoscope 200 with an eyepiece at its proximal end, the endoscope 200 additionally or alternatively may be connected to a monitor. Further details of endoscope 200 may be ascertained by reference to the '504 patent.

Figures 2, 6, 7:
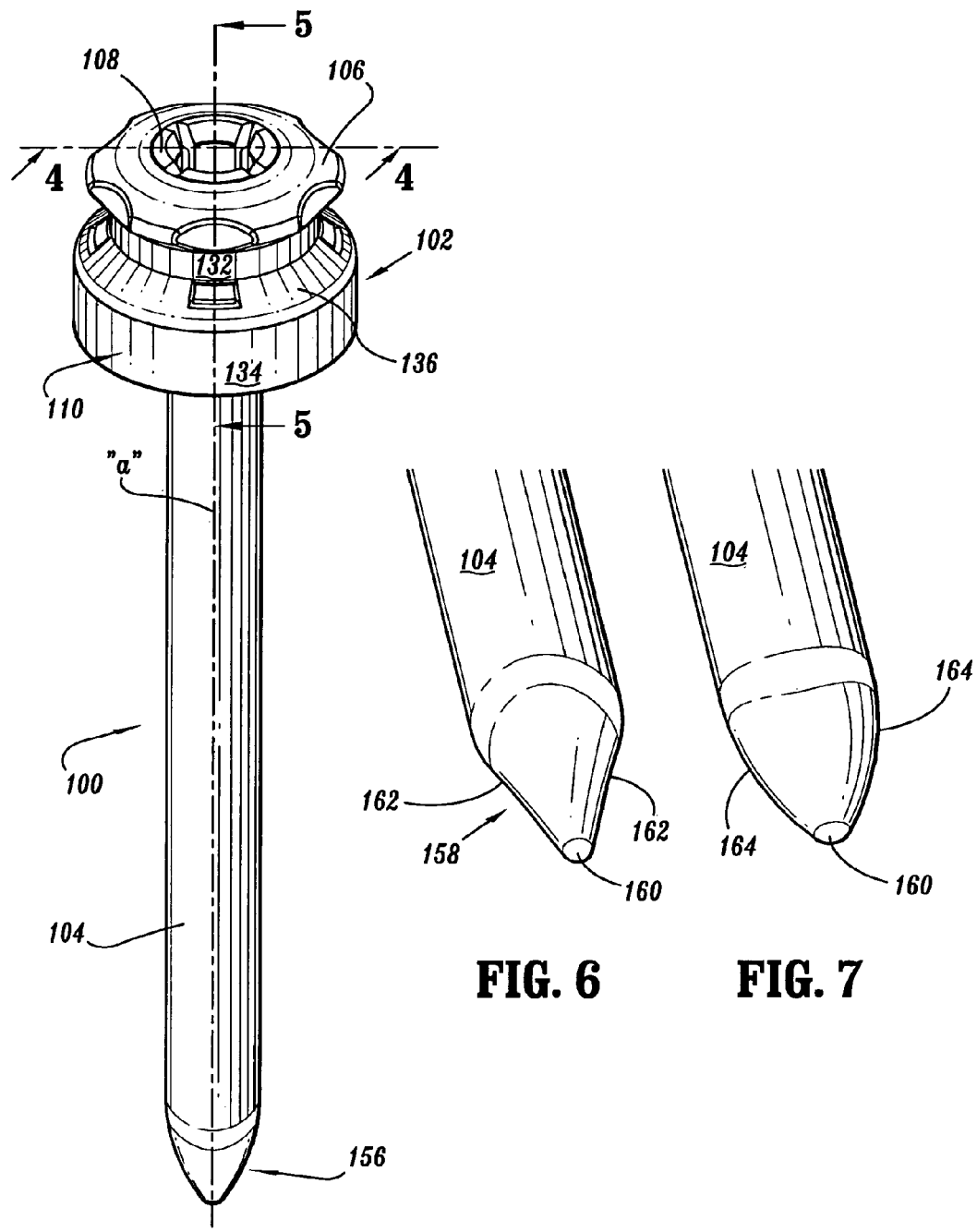
FIG. 2 is a perspective view of the optical access apparatus of the surgical system in accordance with the embodiment of FIG. 1.
FIGS. 6-7 are enlarged perspective views of the penetrating end of the access member of the optical access apparatus in accordance with the embodiment of FIGS. 1-5.
Figure 3:
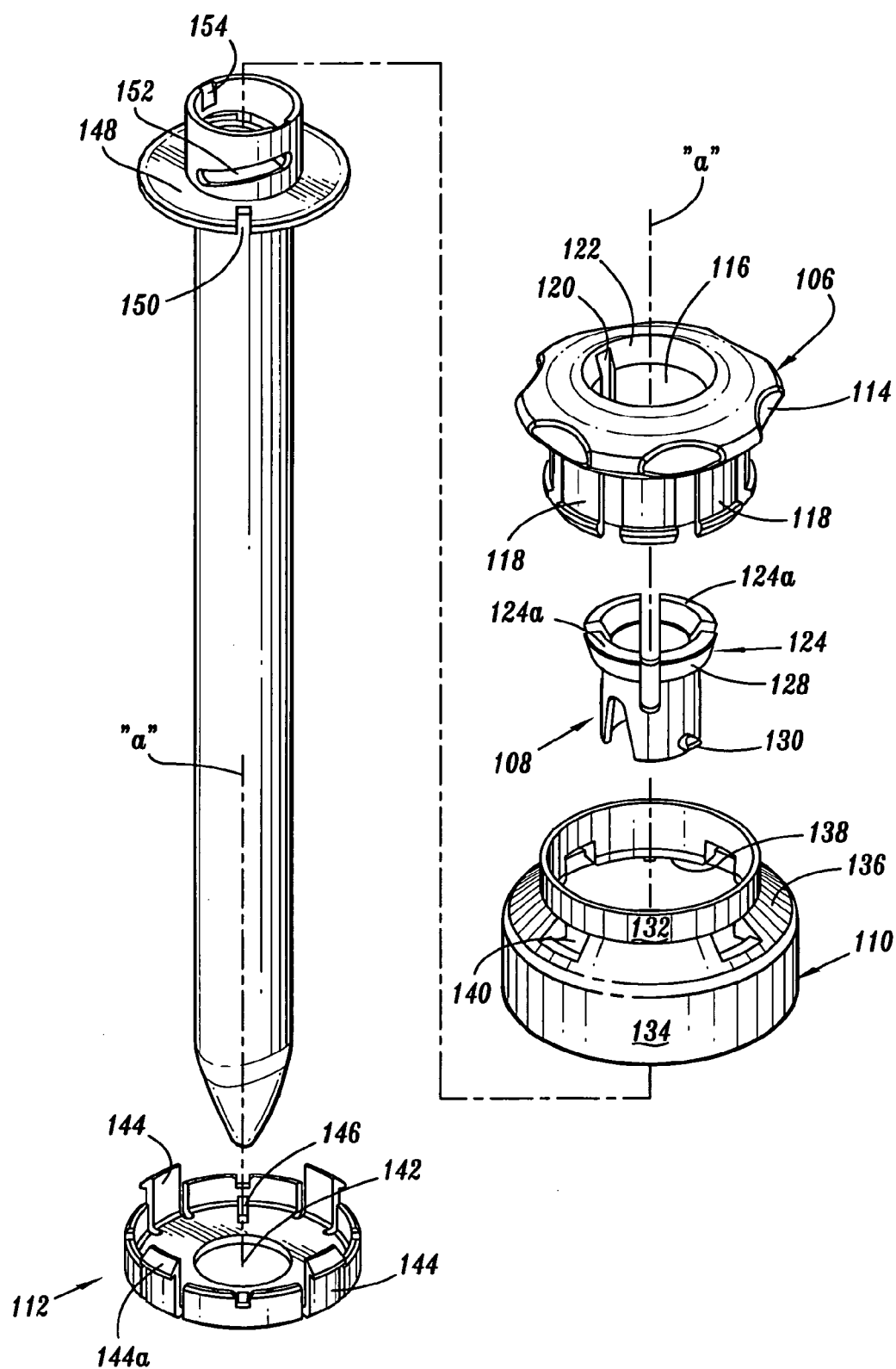
FIG. 3 is a perspective view with parts separated of the optical access apparatus in accordance with the embodiment of FIGS. 1-2, illustrating components of the access member and the housing.
Figure 4:
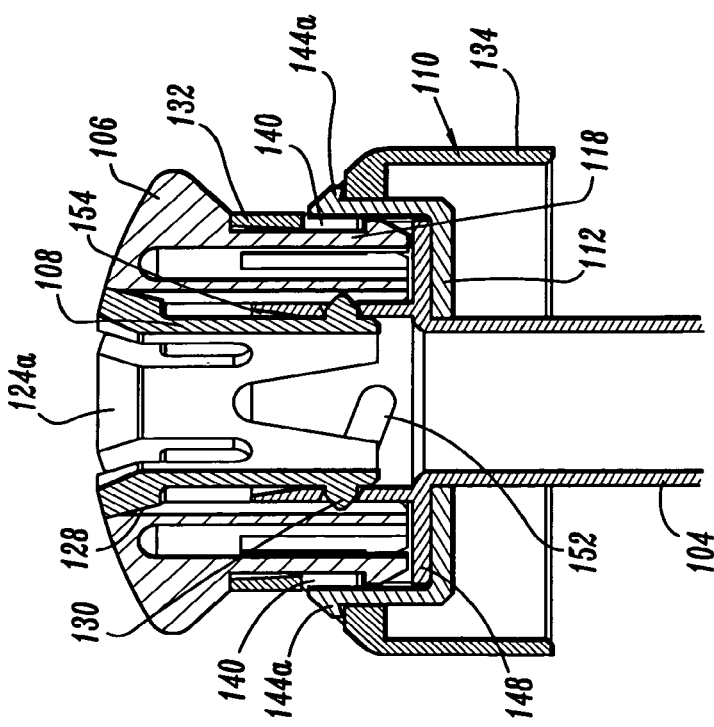
FIG. 4 is a side cross-sectional view of the optical access apparatus in accordance with the embodiment of FIGS. 1-3 and taken along the lines 4-4 of FIG. 2, illustrating the manual member and the collet in an initial position.

Referring now to FIGS. 2-4, optical access apparatus 100 of the system 10 will be discussed. Access apparatus 100 includes housing 102, consisting of several assembled components, and elongate member 104 extending distally from the housing 102. Access apparatus 100 defines longitudinal axis "a". In one preferred embodiment, housing 102 incorporates the following components: manual manipulative member 106, collet 108 which is positioned within the manual member 106, skirt 110 and housing plate 112. As appreciated, these components are assembled together to define a single unit which is subsequently attached to elongate or access member 104.

Manual member 106 is adapted to rotate about the longitudinal axis "a" to secure endoscope 200 in a desired longitudinal position within the access apparatus 100. In this regard, manual member 106 defines an outer scalloped surface 114 advantageously dimensioned to be gripped by the surgeon. Manual member 106 has central aperture 116 extending therethrough which at least partially receives collet 108, and a plurality of axially depending tabs 118 positioned about the longitudinal axis "a" in spaced relation. Tabs 118 are engageable with skirt 110 to mount the manual member 106 to the skirt 110. Manual member 106 also defines a pair of diametrically opposed internal axial slots 120 adjacent central aperture 116. Manual member 106 has internal inclined, e.g., frusto-conical, camming surface 122 at the proximal end of the manual member 106.

Referring still to FIGS. 2-4, collet 108 includes proximal collar 124 which is separated or divided into collar sections 124a by partial slots 126. The outer surface of proximal collar 124 defines inclined or camming surfaces 128 which are obliquely arranged relative to the longitudinal axis "a" of apparatus 100. As to be appreciated, collar sections 124a are adapted to be deflected radially inwardly relative to the axis "a" to frictionally engage endoscope 200 through cooperation of camming surfaces 122, 128 of manual member 106 and collet 108, respectively. Collet 108 further defines a pair of diametrically opposed cam pins 130. Cam pins 130 are received within axial slots 120 of manual member 106 and provide axial movement to collet 108 upon rotation of manual member 106. Cam pins 130 are retained within slots 120 and traverse the slots 120 in a longitudinal direction upon rotational movement of manual member 106 and collet 108.

Figure 5:
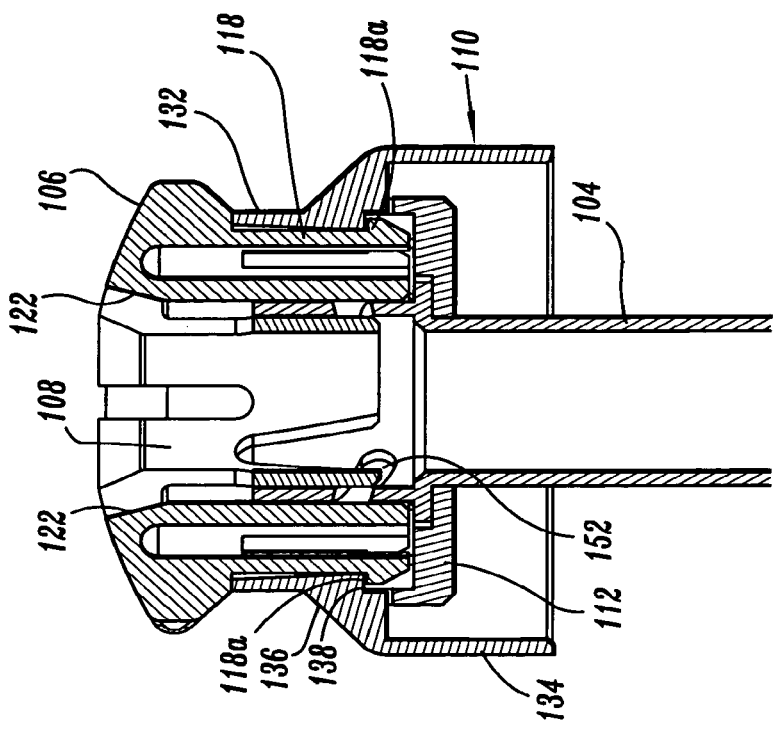
FIG. 5 is a side cross sectional view of the optical access apparatus in accordance with the embodiment of FIGS. 1-4 and taken along the lines 5-5 of FIG. 2.

With reference now to FIGS. 2-5, skirt 110 includes proximal or upper annular wall 132 and lower annular wall 134 interconnected by intermediate sloped wall 136. Skirt 110 defines internal shoulder 138 (FIG. 5) extending transversely relative to axis "a". Shoulder 138 is engaged by locking tabs 118, specifically, transverse shelves 118a of the locking tabs 118, of manual member 106 in the assembled condition of the components to secure skirt 110 and manual member 106. FIG. 5 illustrates in detail the relationship of locking tabs 118 and shoulder 138. Skirt 110 further defines a plurality of rectangular shaped openings 140 extending through sloped wall 136.

Housing plate 112 includes central aperture 142 which is general alignment with the longitudinal axis "a" and axial tabs 144. Tabs 144 possess shelves 144a which are received within rectangular openings 140 of skirt 110 to secure housing plate 112 to the skirt 110. FIG. 4 illustrates in detail the relationship of tabs 144 of housing plate 112 and rectangular openings 140 of skirt 110. Housing plate 112 further defines a plurality of internal projections 146. Projections 146 assist in securing plate 112 to elongate member 104 and to prevent rotational movement of the plate 112 relative to the elongate member 104.

Referring still to FIGS. 2-5, elongate or access member 104 will be discussed. Elongate member 104 includes flange 148 adjacent its proximal end. Flange 148 is generally disc-shaped and defines two opposed radial slots 150. Radial slots 150 accommodate projections 146 of plate 112 in the assembled condition of the components to rotationally fix the components. As shown, flange 148 rests on housing plate 112 when assembled within housing 102. Elongate member 104 further defines a pair of angled cam slots 152 extending completely through the wall of elongate member 104 proximal of flange 148. Cam slots 152 receive cam pins 130 of collet 108 and are dimensioned to permit the pins 130 to traverse the slots 152 upon rotational movement of manual member 106 and the collet 108. As appreciated, during this rotational movement of collet 108, collet 108 is driven in a general downward direction relative to elongate member 104 through the sloped arrangement of cam slots 152. Elongate member 104 further defines a pair of partial internal angled grooves 154 in its interior surface proximal of flange 146. Grooves 154 facilitate assembly of collet 108 within elongate member 104 by receiving cam pins 130 of the collet 108 during insertion of the collet 108 within the elongate member 104.

Referring now to FIGS. 6-7, the distal end portion of elongate member 104 will be discussed. Elongate member 104 defines penetrating end 156 which is characterized by having an irregular shaped nose 158 with rounded tip 160. In particular, nose 158 is generally tapered in configuration defining a complex curved arrangement. In a first profile of nose 158 depicted in FIG. 6, the nose 158 includes opposed concave surfaces 162. In a second profile (rotated) 90° as depicted in FIG. 7, nose 158 defines convex surfaces 164. This alternating concave and convex arrangement provides a substantially reduced profile (in cross-section) compared to conventional conically shaped obturators thereby providing an enhanced ability to penetrate or pass through tissue layers. Various radii of curvature are contemplated. Rounded tip 160, by its arcuate configuration, minimizes the potential of undesired or unintended piercing of tissue. Alternatively, it is envisioned that rounded tip 160 may be more pointed to also pierce tissue if desired.

Penetrating end 156 is substantially hollow to receive the distal end of endoscope 200. Penetrating end 156 is fabricated from a biocompatible transparent material including an optical glass or optical polymeric material and may be either a separate component or integrally formed, e.g., monolithically, with elongate member 104. elongate member 104 may be fabricated from the transparent or opaque material, desirably a biocompatible metal or plastic. Penetrating end 156 is adapted to pass through tissue and may also be capable of cutting or piercing through tissue if desired.

The components of the optical access apparatus may include any suitable biocompatible metal such as stainless steel and titanium and its alloys. Alternatively, the optical access apparatus may include a polymeric material such as polycarbonate, polystyrene, etc . . . . and manufactured via know molding techniques. Elongate member 104 may be transparent throughout its entire length. Alternatively, only penetrating end 156 of elongate member 104 may be transparent.

Figure 9:
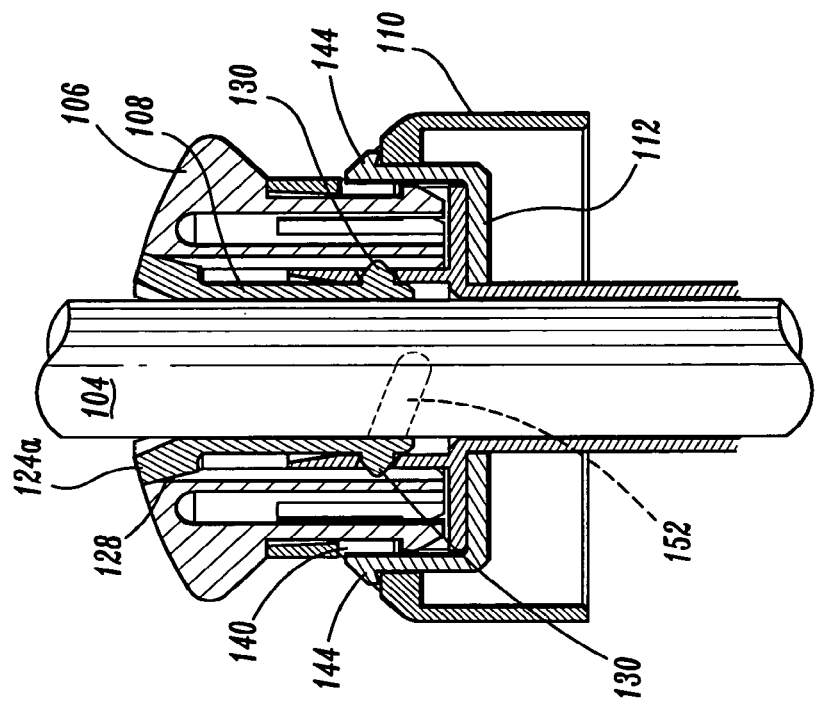
FIG. 9 is a side cross-sectional view similar to the view of FIG. 4 with the endoscope positioned within the optical access apparatus in accordance with the embodiment of FIGS. 1-8.
Figure 8:
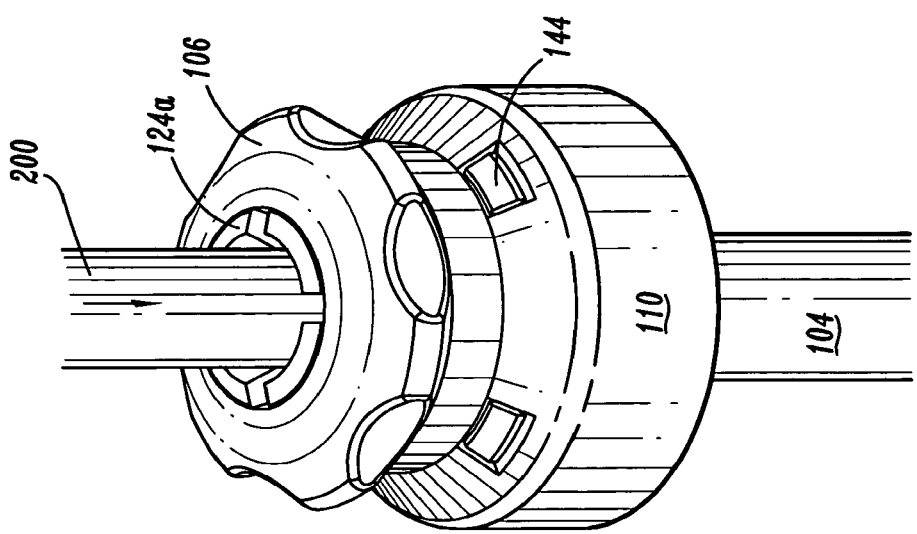
FIG. 8 is an enlarged perspective view of the optical access apparatus with the endoscope positioned therein in accordance with the embodiment if FIGS. 1-7, illustrating the manual member in an initial condition.

The use and function of the system 10 will now be discussed. In laparoscopic surgery, the abdominal cavity is insufflated with a suitable biocompatible gas such as, e.g., $CO_2$ gas, to insufflate the body cavity and lift the body cavity wall away from the internal organs therein. The insufflation may be performed with an insufflation needle or similar device as is conventional in the art. Thereafter, an incision is made in the outer epidermal surface of the abdominal cavity. The incision is preferably small, for example, within a range from 2 to 7 mm, and may be made with a scalpel etc. Thereafter, endoscope 200 of system 10 is positioned within optical access apparatus 100 and advanced such that the distal window of the endoscope 200 is adjacent the nose 158 of elongate member 104. FIGS. 8-9 illustrate the relationship of endoscope 200 within optical access apparatus 10. In FIGS. 8-9, manual member 106 and collet 108 are in an initial position permitting endoscope 200 to advance within elongate member 104. When endoscope 200 is at the desired position within access apparatus 100, e.g., when the distal objective of the endoscope 200 is within or adjacent nose 158 of elongate member 104, the endoscope 200 is then secured at the desired location by manipulating the holding mechanism as discussed below.

Figure 11:
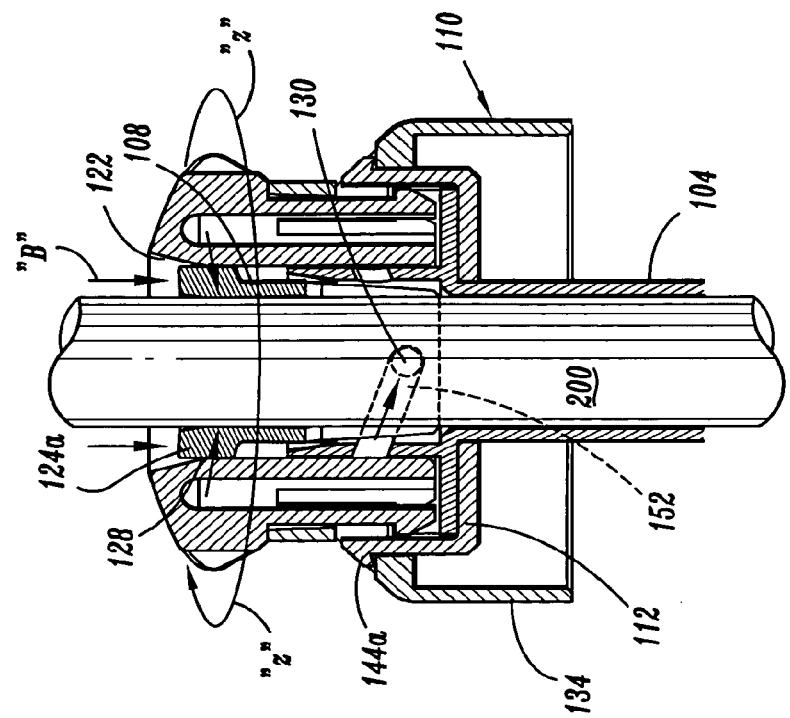
FIG. 11 is a view similar to the view of FIG. 9 further illustrating the collet securing the endoscope upon movement of the manual member to the actuated position in accordance with the embodiment of FIGS. 1-10.
Figure 10:
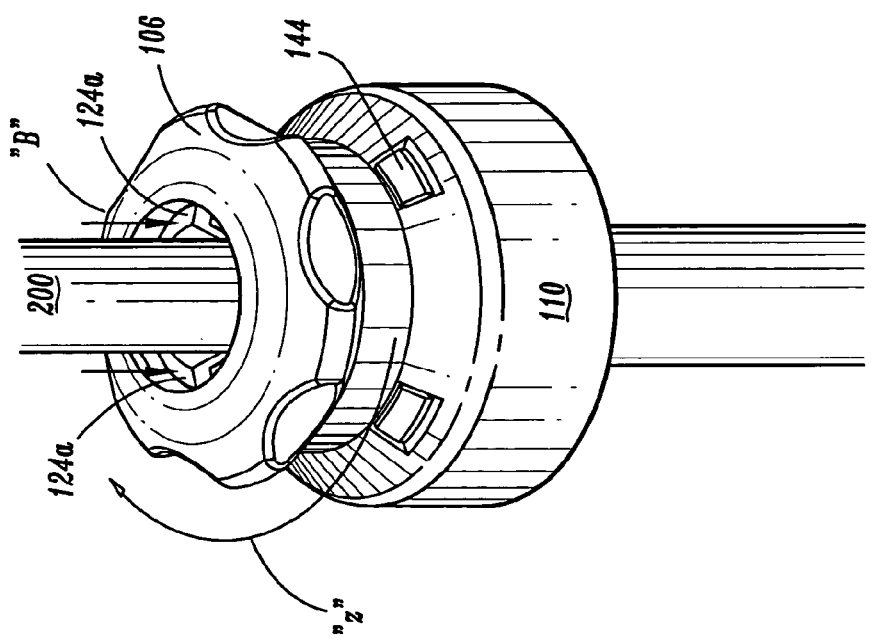
FIG. 10 is a view similar to the view of FIG. 8 illustrating the manual member of the optical access apparatus in an actuated position securing the endoscope in accordance with the embodiment of FIGS. 1-9.

With reference now to FIGS. 10-11, to secure endoscope 200, manual member 106 is rotated in the direction of the directional arrows "Z". Rotation of manual member 106 causes corresponding rotation of collet 108 through the receptive arrangement of cam pins 130 of the collet 108 within internal slots 120 of the manual member 106. Concurrently with the rotation of collet 108, cam pins 130 traverse cam slots 152 of elongate member 104, which drives collet 108 in a distal or downward direction as shown by directional arrows "B". It is noted that cam pins 130 also traverse internal slots 120 (i.e., move in a distal longitudinal direction) of manual member 106 to permit collet 108 to move distally relative to manual member 106. During distal movement of collet 108, camming surface 122 of manual member 106 cooperates with camming surfaces 128 of collar sections 124a to cause the collar sections 124a to flex inwardly and compressively engage the endoscope 200 and frictionally secure the endoscope 200 within access apparatus 100.

Figure 12:
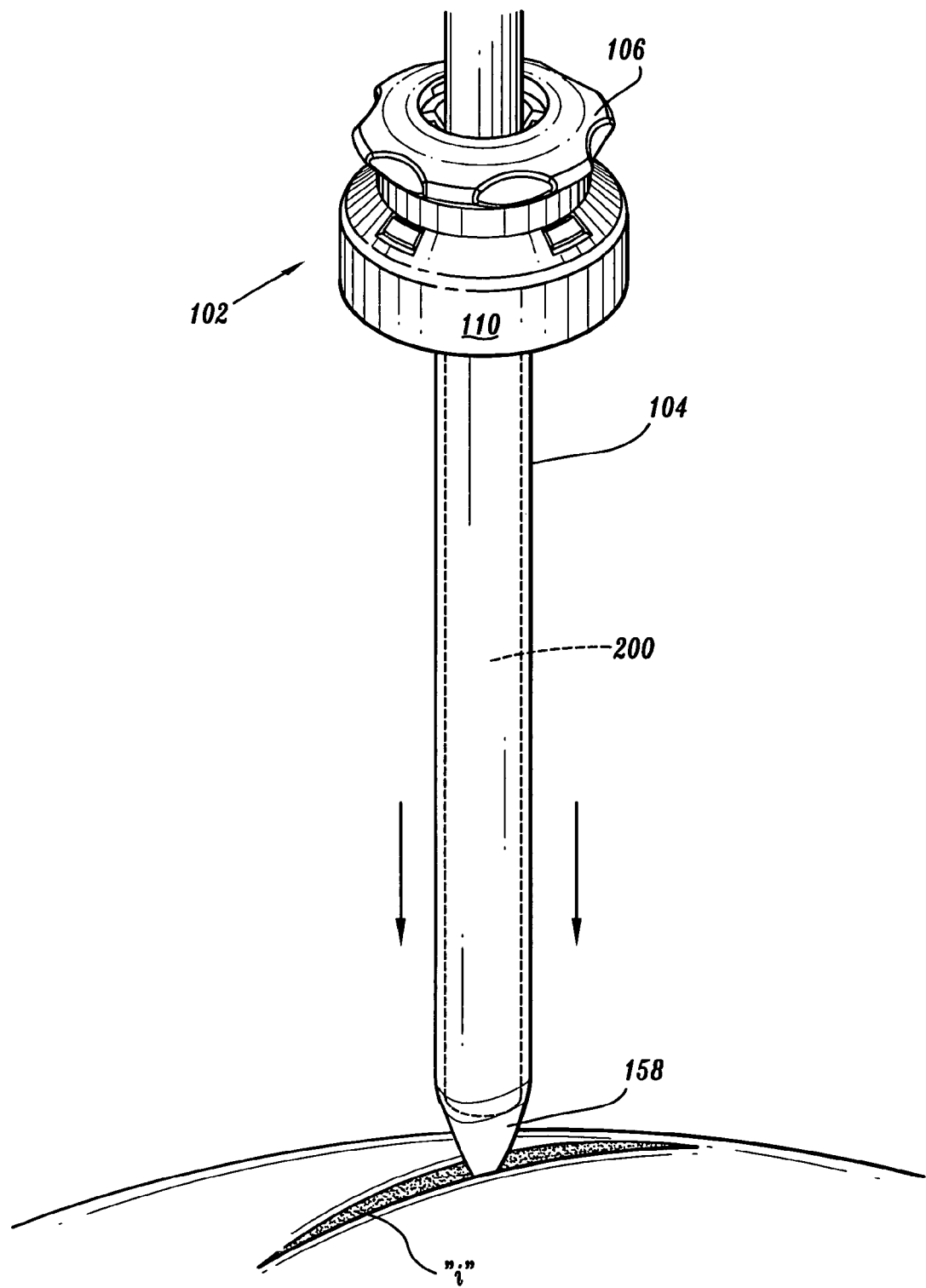
FIG. 12 is a perspective view illustrating an endoscope positioned within the optical access apparatus and accessing body tissue.

With reference to FIG. 12, the assembled system 10 is then introduced within the small incision "i" by positioning nose 158 of elongate member 104 within the incision and advancing the system 10 through the incision and the underlying tissue structure. Nose 158 is advantageously dimensioned to penetrate and dissect the tissue along its path desirably in a non-traumatic fashion. During advancement of system 10, endoscope 200 is utilized to view the path along which the system is advanced to ensure that any underlying tissue or organ site is prevented from contact with the access apparatus 100 and also to confirm entry within the body cavity. Once system 10 is positioned at the desired location relative to the abdominal cavity, endoscope 200 may be used to monitor the desired surgical procedure being performed within the cavity. In the alternative, endoscope 200 may be inserted into and secured in the access apparatus 100 after the access apparatus 100 has been used to penetrate tissue.

Figure 13:
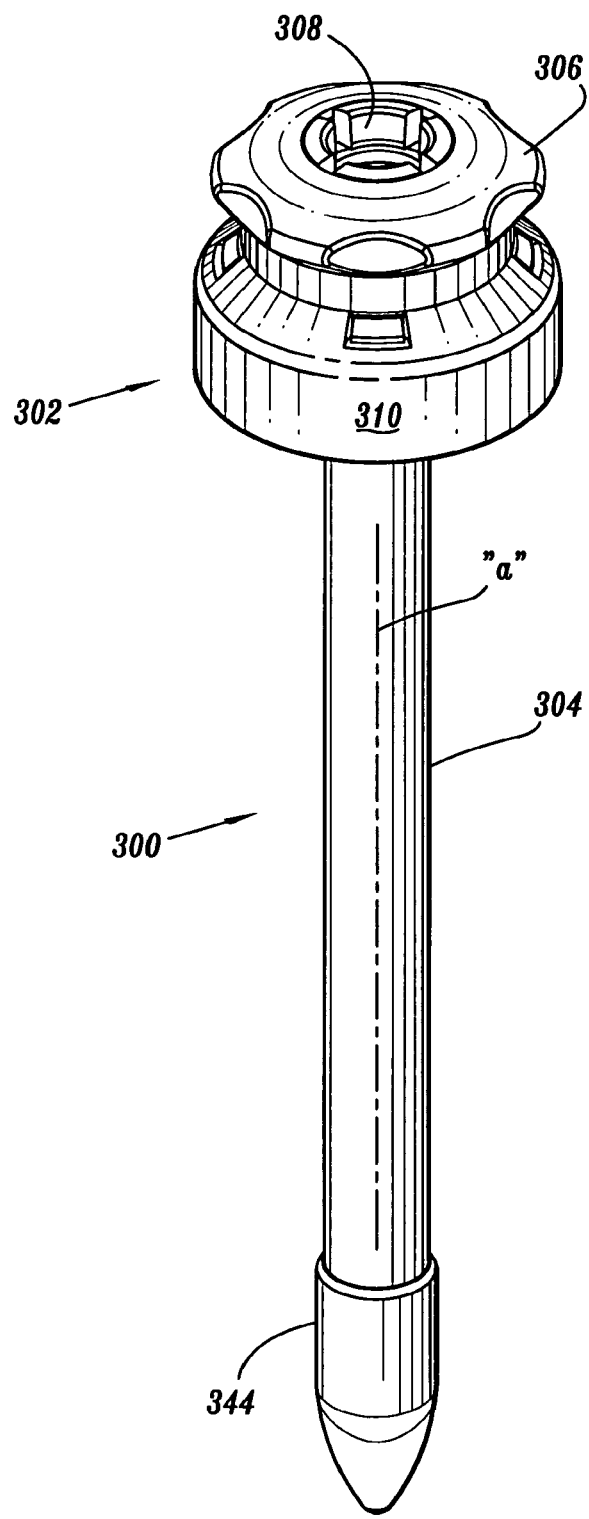
FIG. 13 is a perspective view of an alternate optical access apparatus for use with the system of the present disclosure.
Figure 14:
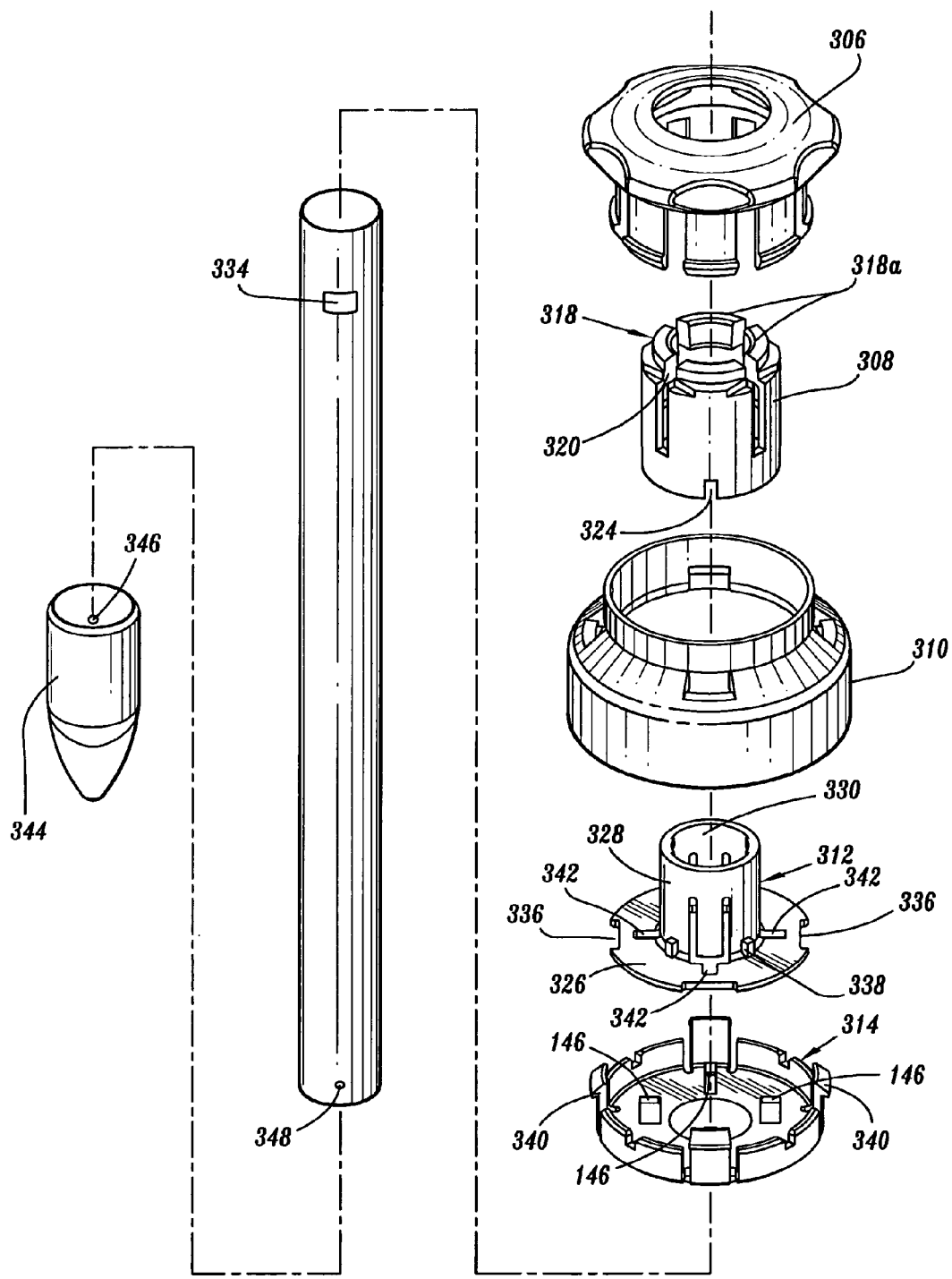
FIG. 14 is a perspective view with parts separated of the optical access apparatus in accordance with the embodiment of FIG. 13, illustrating components of the access member and the housing.
Figure 16:
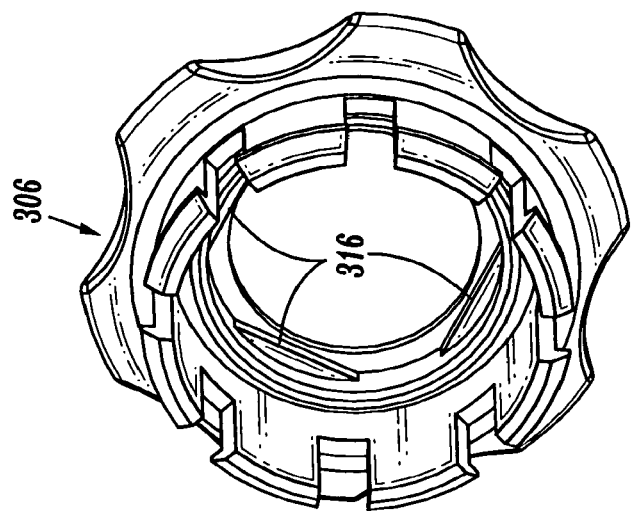
FIG. 16 is a perspective view of the manual member of the optical access apparatus in accordance with the embodiment if FIGS. 13-15, illustrating the camming surfaces of the manual member.
Figure 15:
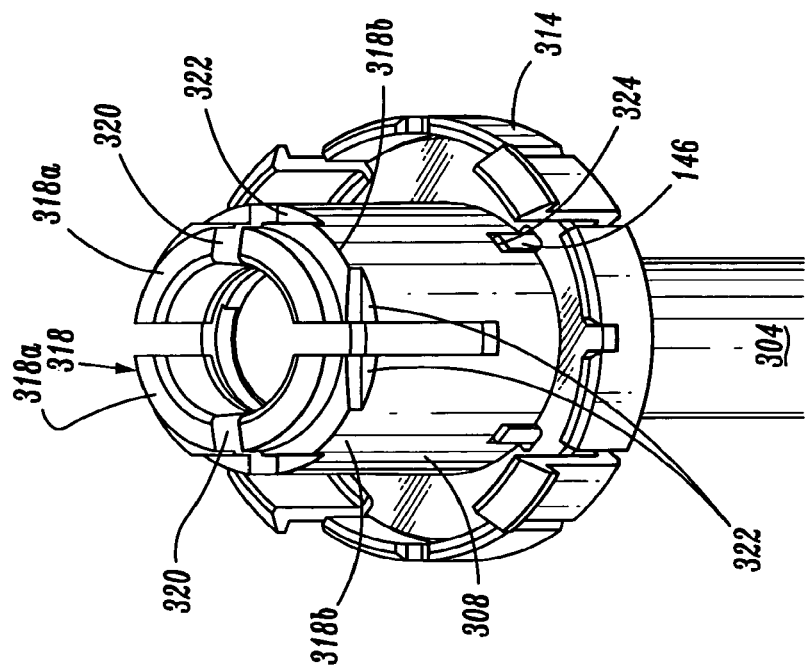
FIG. 15 is a perspective view of the collet mounted to the elongate member of the optical access apparatus in accordance with the embodiment of FIGS. 13-14.

Referring now to FIGS. 13-15, there is illustrated an alternate embodiment of the optical access apparatus for use in the system 10 of the present disclosure. Optical access apparatus 300 is substantially similar to access apparatus 100 of FIGS. 1-12, and possesses housing 302 and elongate member 304. Housing 302 consists of manual member 306, collet 308, skirt 310, flange extension 312 and housing plate 314 with the components assembled together to define a single unit. Manual member 306 is substantially identical to manual member 106 of access apparatus 100 but further defines internal cam shelves 316 (four are shown) as best depicted in FIG. 16, which replaces camming surfaces 122 of manual member 106 of the aforedescribed access apparatus 100. Manual member 306 is adapted to rotate about longitudinal axis "a" and relative to collet 308. In this embodiment, collet 308 is stationary within housing 302, i.e., it does not rotate with manual member 306.

As best depicted in FIGS. 14-15, collet 308 includes proximal collar 318 having four collar sections 318a with adjacent sections 318a separated by slots 320. (In FIG. 15, housing 302 is shown without manual member 306 mounted to collet 308.) Each collar section 318a has opposed outer grooves 322 arranged in a manner such that respective grooves 322 of adjacent collar sections 318a, in effect, define a recess across the adjacent sections 318a. Grooves or recesses 322 accommodate cam shelves 316 of manual member 306 when in the initial position of manual member 306. Outer cam surfaces 318b are defined between grooves 322. As will be appreciated, during rotation of manual member 306, cams shelves 316 of manual member 306 traverse grooves 322 and engage cam surfaces 318b to bias collar sections 318a inwardly into secured engagement with endoscope 200. Collet 318 further includes lower slots 324 in its outer surface which serve to secure the collet 318 within housing 302.

Figure 18:
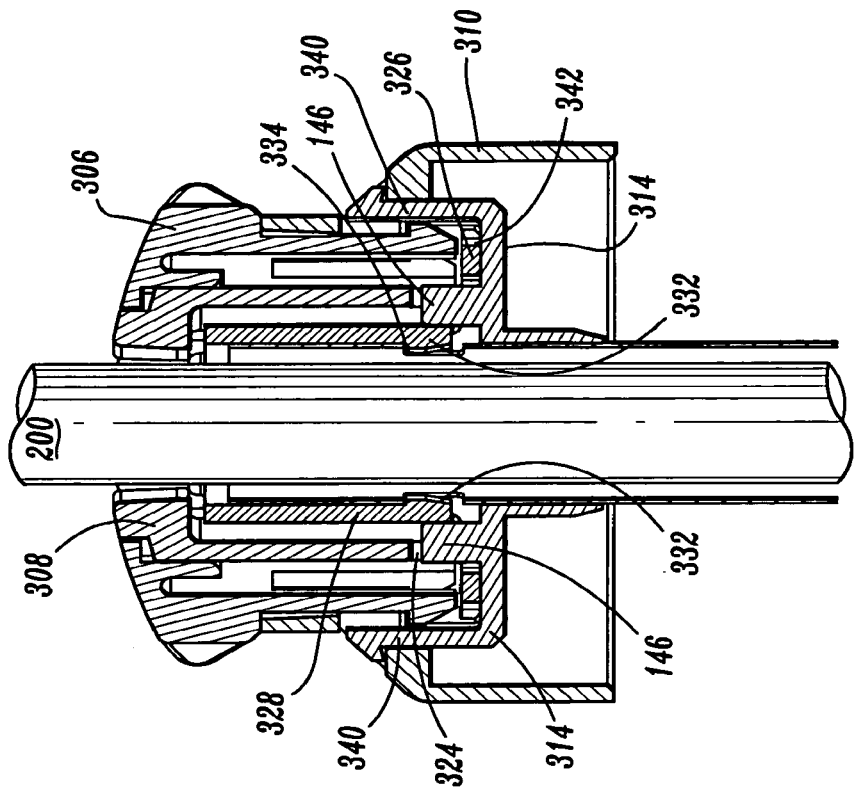
FIG. 18 is a side cross-sectional view of the optical access apparatus with the endoscope positioned therein in accordance with the embodiment of FIGS. 13-17, illustrating the manual member in an initial position.
Figure 17:
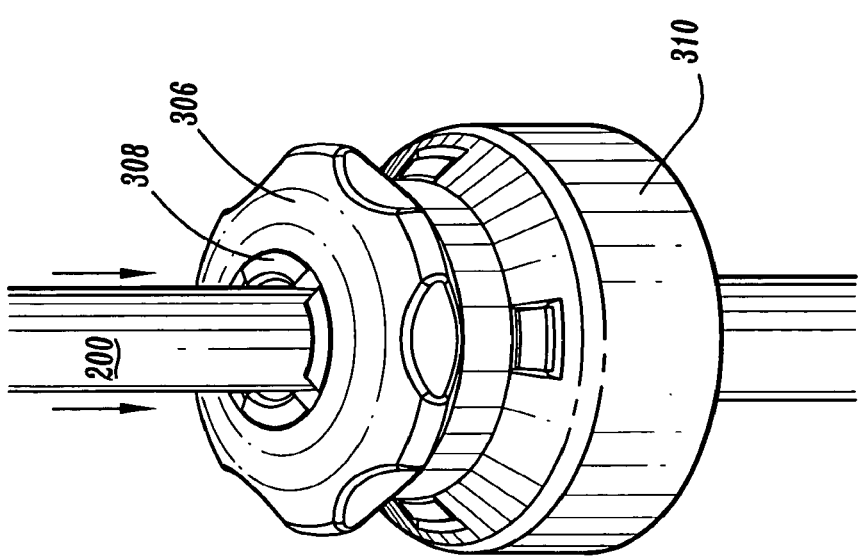
FIG. 17 is an enlarged perspective view of the optical access apparatus with the endoscope positioned therein in accordance with the embodiment if FIGS. 13-16, illustrating the manual member in an initial condition.

Referring now to FIGS. 17-19, in conjunction with FIGS. 13-14, skirt 310 and housing plate 314 are substantially identical to the corresponding counterparts of the embodiment of FIGS. 1-12, and reference is made to the foregoing description for detailed discussion of the structure and function thereof. However, with this embodiment, it is noted housing plate 314 includes two pairs of projections 146. Projections 146 of housing plate 314 are received within lower slots 324 of collet 308 so as to secure and prevent rotational movement of the collet 308.

Flange extension 312 replaces flange of the embodiment of FIGS. 1-12, and is a separate component attached to elongate member 304 by mechanical means. Flange extension 312 includes flange plate 326 and flange collar 328 extending from the flange plate 326. Flange collar 328 defines central aperture 330 to permit passage of the endoscope 200. Flange collar 328 includes internal shelves 332 which are received within corresponding openings 334 in the proximal end of elongate member 304 to fix the flange extension 312 to the elongate member 304. (FIG. 18) Flange plate 326 rests on housing plate 314 and defines a plurality of rectangular grooves 336 in its periphery and a plurality of spacers 338 at the intersection with flange collar 328. Grooves 336 accommodate portions of locking tabs 340 extending from housing plate 314. Spacers 338 serve to align collet 308. Flange plate 328 has two pairs of opposed slots 342 which accommodate projections 146 of housing plate 314.

With reference again to FIGS. 13-14, elongate member 304 is substantially identical to elongate member 104 of the embodiment of FIGS. 1-12, but, incorporates a separate penetrating end 344. In this regard, penetrating end 344 is attached to elongate member 304 through conventional means including adhesives, cements, bayonet coupling, or in a preferred embodiment, a snap fit arrangement consisting of a plurality of internal projections 346 extending within elongate member 304, which are received within correspondingly dimensioned openings 348 of elongate member 304. Other means for connecting penetrating end are also envisioned. Penetrating end 344 is transparent as discussed hereinabove and is preferably identical in configuration to the penetrating end of the embodiment of FIGS. 1-12.

Figure 22:
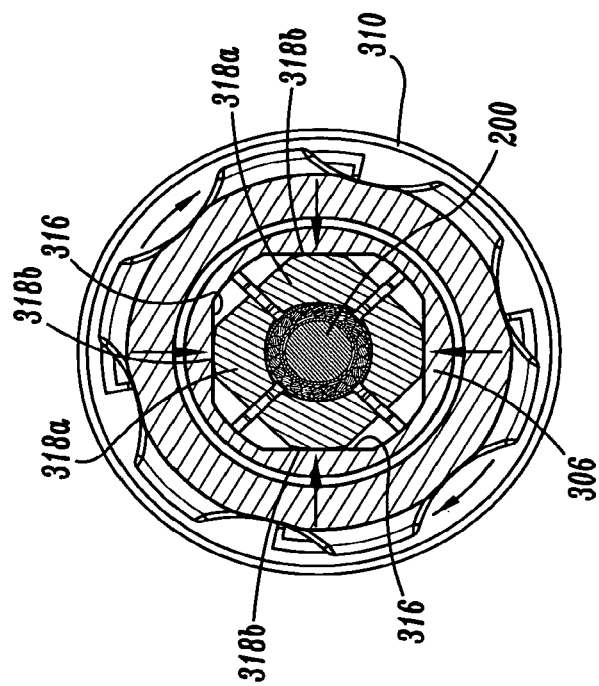
FIG. 22 is a view similar to the view of FIG. 19 further illustrating movement of the manual member to the actuated position in accordance with the embodiment of FIGS. 13-21.
Figure 21:
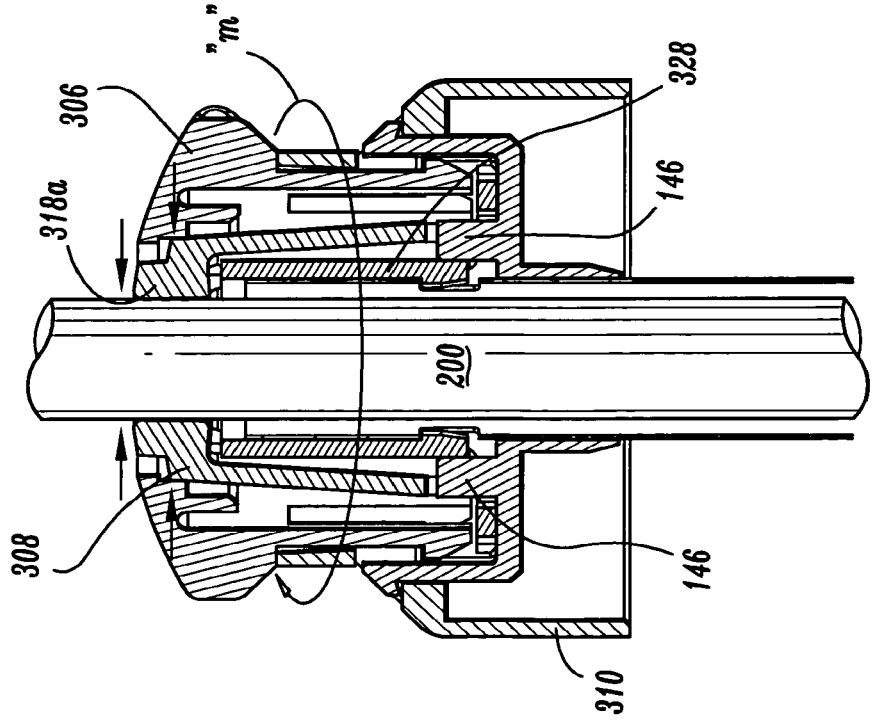
FIG. 21 is a view similar to the view of FIG. 18 further illustrating movement of the manual member to the actuated position in accordance with the embodiment of FIGS. 13-20.

Referring now to FIGS. 20-22, the function and use of optical access apparatus 300 will be discussed. The abdominal cavity is insufflated and the incision is formed in the epidermal tissue. Endoscope 200 is positioned within access apparatus 300 and advanced to a portion where the distal end of the endoscope is positioned within penetrating end 344. Manual member 306 is rotated about the longitudinal axis "x" in the direction of the rotational arrow 'm' and relative to collet 308. During this movement, collet 308 remains stationary while internal cam shelves 316 of manual member 306 traverse grooves 322 of collet 308 to engage outer cam surfaces 318b of collar sections 318a. This camming action drives collar sections 318a inwardly to the position depicted in FIGS. 21 and 22. In this position, collar sections 318a securely engage the endoscope 200. The system 10 is then used in similar manner to that described in the embodiment of FIGS. 1-12. Alternatively, endoscope 200 is inserted into the access apparatus 300 and secured after the access apparatus has penetrated tissue.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An optical access apparatus for reception of an endoscope to permit visualization during passage through tissue, which comprises:
   an access member dimensioned for insertion through body tissue and having proximal and distal ends, the access member defining a longitudinal axis and having a longitudinal opening for receiving the endoscope, the access member having a penetrating end adjacent the distal end adapted to pass through tissue, the penetrating end being at least partially transparent to permit visualization of tissue with the endoscope;
   a locking collet coaxially mounted relative to the longitudinal axis of the access member, the locking collet having internal surfaces, defining an internal passage to permit passage of the endoscope, the locking collet including a proximal collar which is divided into collar sections by partial slots, the collar sections adapted to be deflected radially inwardly relative to the longitudinal axis of the access member; and
   a manual member coaxially mounted about the locking collet, the manual member adapted for rotational movement about the longitudinal axis, and cooperating to drive the locking collet in a distal direction relative to and along the longitudinal axis of the access member and deflecting the collar sections radially inwardly to reduce an internal dimension of the internal passage of the locking collet to thereby cause the internal surfaces of the locking collet to securely engage the endoscope, the manual member being fixed from longitudinal movement relative to the access member.

2. The optical access apparatus according to claim 1 wherein the locking collet includes a cam pin extending outwardly therefrom and wherein the access member includes a cam slot for receiving the cam pin whereby rotational movement of the manual member causes the cam pin to traverse the cam slot to cause the locking collet to move in the distal direction relative to the access member.

3. The optical access apparatus according to claim 1 wherein the manual member includes internal compressive surfaces adapted to engage the locking collet during distal movement of the locking collet to reduce the internal dimension of the internal passage of the locking collet.

4. An access apparatus, which comprises:
   an access member dimensioned for insertion through body tissue and having proximal and distal ends, the access member defining a longitudinal axis and having a longitudinal opening for receiving an instrument;
   a locking collet coaxially mounted relative to the longitudinal axis of the access member, the locking collet having internal surfaces defining an internal passage to permit passage of the instrument, the locking collet including a proximal collar which is divided into collar sections by partial slots, the collar sections adapted to be deflected radially inwardly relative to the longitudinal axis of the access member; and
   a manual member coaxially mounted about the locking collet, the manual member adapted for rotational movement about the longitudinal axis, and cooperating to drive the locking collet in a distal direction relative to and along the longitudinal axis of the access member whereby the collar sections are deflected radially inwardly to reduce an internal dimension of the internal passage of the locking collet to thereby cause the internal surfaces of the locking collet to securely engage the instrument.

5. The access apparatus according to claim 4 wherein the access member includes a or cam slot and the locking collet includes a cam pin, the cam pin and the cam slot cooperating to drive the locking collet in the distal direction upon rotation of the manual member.

6. The access apparatus according to claim 5 wherein the cam pin is dimensioned to extend radially outwardly relative to the longitudinal axis and wherein the manual member includes an axial slot, the cam pin traversing the axial slot during movement of the locking collet in the distal direction.

7. The access apparatus according to claim 6 wherein the access member includes the cam slot, the cam pin of the locking collet traversing the cam slot of the access member upon rotation of the locking collet to be driven in the distal direction.

8. The access apparatus according to claim 7 wherein the manual member is fixed from longitudinal movement relative to the access member.

9. The access apparatus according to claim 8 the manual member includes internal compressive surfaces adapted to engage external surfaces of the locking collet during distal movement of the locking collet to reduce the internal dimension of the internal passage of the locking collet.

* * * * *